[12] United States Patent
Wolf

(10) Patent No.: US 9,445,924 B2
(45) Date of Patent: Sep. 20, 2016

(54) TUBULAR METAL PROSTHESIS AND METHOD OF MAKING IT

(75) Inventor: Jaqueline Wolf, Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 1180 days.

(21) Appl. No.: 12/373,116

(22) PCT Filed: Jul. 10, 2007

(86) PCT No.: PCT/EP2007/057041
§ 371 (c)(1),
(2), (4) Date: Jul. 14, 2009

(87) PCT Pub. No.: WO2008/006830
PCT Pub. Date: Jan. 17, 2008

(65) Prior Publication Data
US 2010/0070018 A1 Mar. 18, 2010

(51) Int. Cl.
A61F 2/06 (2013.01)
A61F 2/82 (2013.01)
A61F 2/915 (2013.01)
B23K 31/02 (2006.01)

(52) U.S. Cl.
CPC .............. A61F 2/82 (2013.01); A61F 2/915 (2013.01); B23K 31/02 (2013.01); A61F 2002/91591 (2013.01); A61F 2220/0058 (2013.01); A61F 2250/0096 (2013.01); A61F 2250/0098 (2013.01); B23K 2203/18 (2013.01); Y10T 29/49826 (2015.01)

(58) Field of Classification Search
CPC .......... A61F 2250/0098; A61B 19/54; A61M 2025/09166; A61M 25/0108
USPC ............................. 623/1.11, 1.36, 1.15, 1.34
See application file for complete search history.

(56) References Cited

U.S. PATENT DOCUMENTS

| 5,741,327 | A | 4/1998 | Frantzen |
| 5,759,192 | A | 6/1998 | Saunders |
| 5,861,027 | A | 1/1999 | Trapp |
| 5,868,783 | A | 2/1999 | Tower |
| 6,022,374 | A | 2/2000 | Imran |
| 6,056,187 | A | 5/2000 | Acciai et al. |
| 6,293,966 | B1 | 9/2001 | Frantzen |
| 6,379,381 | B1 | 4/2002 | Hossainy et al. |

(Continued)

FOREIGN PATENT DOCUMENTS

| DE | 04130431 A1 | 3/1993 |
| DE | 29621207 U1 | 1/1997 |

(Continued)

OTHER PUBLICATIONS

Database Wikipedia, Sep. 11, 2007, "lumen (anatomy)"; xp002453737, abstract.

(Continued)

Primary Examiner — Christian Sevilla
Assistant Examiner — Seema Mathew
(74) Attorney, Agent, or Firm — C.R. Bard Intellectual Property Buchalter Nemer, a PC

(57) ABSTRACT

For welding a polished component of one metal to a polished prosthesis of another metal, ramp surfaces are used, to compensate for loss of precise dimensions of the two components at the surfaces that face each other at the weld interface, during the respective polishing procedures for the two metals.

6 Claims, 1 Drawing Sheet

(56) References Cited

U.S. PATENT DOCUMENTS

| | | | |
|---|---|---|---|
| 6,540,777 B2 | 4/2003 | Stenzel et al. | |
| 7,462,190 B2 | 12/2008 | Lombardi | |
| 2002/0193869 A1 | 12/2002 | Dang | |
| 2003/0144725 A1* | 7/2003 | Lombardi | 623/1.13 |
| 2004/0015228 A1* | 1/2004 | Lombardi et al. | 623/1.18 |
| 2004/0015229 A1 | 1/2004 | Fulkerson et al. | |
| 2004/0073291 A1 | 4/2004 | Brown et al. | |
| 2004/0236409 A1 | 11/2004 | Pelton et al. | |
| 2004/0254637 A1 | 12/2004 | Yang et al. | |
| 2005/0049682 A1 | 3/2005 | Leanna et al. | |
| 2005/0060025 A1* | 3/2005 | Mackiewicz et al. | 623/1.34 |
| 2005/0172471 A1 | 8/2005 | Vietmeier | |
| 2006/0216431 A1 | 9/2006 | Kerrigan | |
| 2007/0219624 A1 | 9/2007 | Brown et al. | |
| 2009/0200360 A1 | 8/2009 | Wack | |
| 2010/0070021 A1 | 3/2010 | Wack et al. | |
| 2010/0114298 A1 | 5/2010 | Dorn et al. | |

FOREIGN PATENT DOCUMENTS

| | | |
|---|---|---|
| DE | 19728337 A1 | 1/1999 |
| DE | 29904817 U1 | 5/1999 |
| DE | 10201151 A1 | 7/2003 |
| EP | 0709068 A2 | 5/1996 |
| EP | 0800800 A1 | 10/1997 |
| EP | 0847733 A1 | 6/1998 |
| EP | 1157673 A2 | 11/2001 |
| EP | 1212991 A2 | 6/2002 |
| EP | 1255507 A1 | 11/2002 |
| EP | 1356789 A1 | 10/2003 |
| EP | 1488763 A2 | 12/2004 |
| FR | 2626046 A1 | 7/1989 |
| GB | 453944 A | 9/1936 |
| JP | 07315147 A | 12/1995 |
| WO | 9503010 A1 | 2/1995 |
| WO | 9733534 A1 | 9/1997 |
| WO | 9915108 A1 | 1/1999 |
| WO | 0064375 A1 | 11/2000 |
| WO | 0158384 A1 | 8/2001 |
| WO | 0215820 A2 | 2/2002 |
| WO | WO02/15820 | 2/2002 |
| WO | 03101343 A1 | 12/2003 |
| WO | 2004058384 A1 | 7/2004 |
| WO | WO2005/072652 | 8/2005 |
| WO | 2008022950 A1 | 2/2008 |
| WO | 2008068279 A1 | 6/2008 |
| WO | 2008101987 A1 | 8/2008 |

OTHER PUBLICATIONS

International Search Report for WO2008/006830 published Jan. 17, 2008 for priority document PCT/EP2007/057041 filed Jul. 10, 2007/.
International Application No. PCT/EP2001/009467 International Preliminary Examination Report Sep. 17, 2002.
International Application No. PCT/EP2001/009467 International Search Report dated Feb. 18, 2002.
International Application No. PCT/EP2007/057041 filed Jul. 10, 2007 International Preliminary Report on Patentability dated Jan. 13, 2009.
International Application No. PCT/EP2007/057041 filed Jul. 10, 2007 Written Opinion Jan. 10, 2009.
International Application No. PCT/EP2007/058416 filed Aug. 14, 2007 International Preliminary Report on Patentability dated Feb. 24, 2009.
International Application No. PCT/EP2007/058416 filed Aug. 14, 2007 International Search Report dated Nov. 22, 2007.
International Application No. PCT/EP2007/058416 filed Aug. 14, 2007 Written Opinion dated Feb. 23, 2009.
International Application No. PCT/EP2007/063347 filed Dec. 5, 2007 International Search Report dated Jun. 10, 2009.
International Application No. PCT/EP2007/063347 filed Dec. 5, 2007 Written Opinion dated Jun. 10, 2009.
International Application No. PCT/EP2007/063347 filed on Dec. 5, 2007 International Search Report dated Feb. 4, 2008.
International Application No. PCT/EP2008/052121 filed Feb. 21, 2008 International Preliminary Report on Patentability dated Aug. 26, 2009.
International Application No. PCT/EP2008/052121 filed Feb. 21, 2008 International Search Report dated May 19, 2008.
International Application No. PCT/EP2008/052121 filed Feb. 21, 2008 Written Opinion dated May 9, 2008.
U.S. Appl. No. 10/362,040, filed Jun. 27, 2003 Advisory Action dated Jan. 9, 2009.
U.S. Appl. No. 10/362,040, filed Jun. 27, 2003 Advisory Action dated Nov. 29, 2006.
U.S. Appl. No. 10/362,040, filed Jun. 27, 2003 Office Action dated Aug. 18, 2008.
U.S. Appl. No. 10/362,040, filed Jun. 27, 2003 Office Action dated Aug. 2, 2006.
U.S. Appl. No. 10/362,040, filed Jun. 27, 2003 Office Action dated Dec. 10, 2007.
U.S. Appl. No. 10/362,040, filed Jun. 27, 2003 Office Action dated Feb. 23, 2010.
U.S. Appl. No. 10/362,040, filed Jun. 27, 2003 Office Action dated Jan. 10, 2006.
U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
U.S. Appl. No. 12/438,330, filed Feb. 20, 2009 Office Action dated Mar. 16, 2010.
EP 07802603.6 filed Aug. 14, 2007 Office Action dated Dec. 13, 2010.
U.S. Appl. No. 10/362,040, filed Jun. 27, 2003 Advisory Action dated Dec. 16, 2010.
U.S. Appl. No. 10/362,040, filed Jun. 27, 2003 Final Office Action dated Aug. 30, 2010.
U.S. Appl. No. 12/438,330, filed Feb. 20, 2009 Advisory Action dated Oct. 14, 2010.
U.S. Appl. No. 12/438,330, filed Feb. 20, 2009 Office Action dated Aug. 5, 2010.
U.S. Appl. No. 10/362,040, filed Jun. 27, 2003 Notice of Allowance dated Jun. 22, 2011.
U.S. Appl. No. 12/438,330, filed Feb. 20, 2009 Office Action dated Mar. 4, 2011.
U.S. Appl. No. 12/517,096, filed Jun. 1, 2009 Office Action dated May 6, 2011.
U.S. Appl. No. 12/438,330, filed Feb. 20, 2009 Final Office Action dated Aug. 11, 2011.
EP 07787316.4 filed Jul. 10, 2007 Examination Report dated Dec. 23, 2011.

* cited by examiner

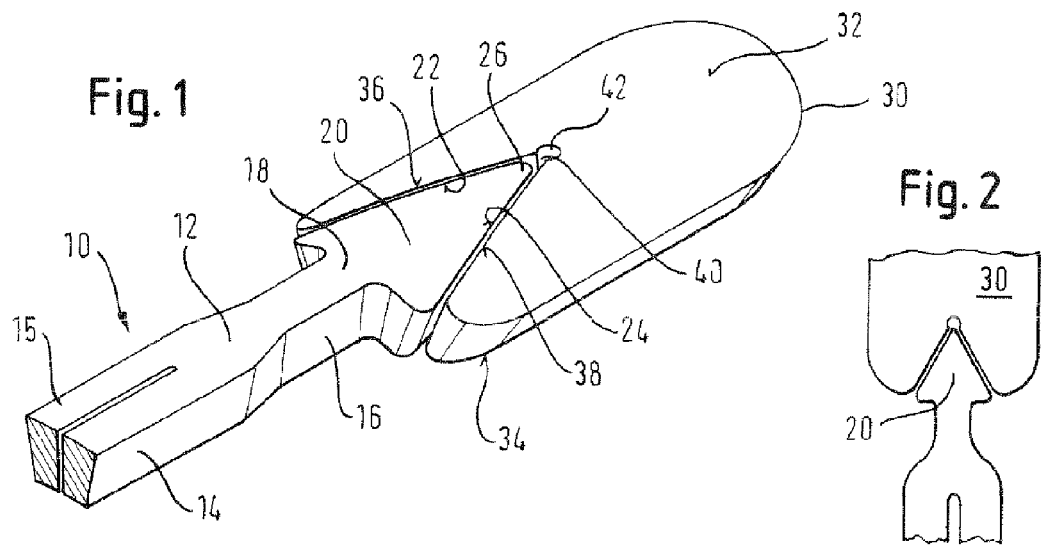
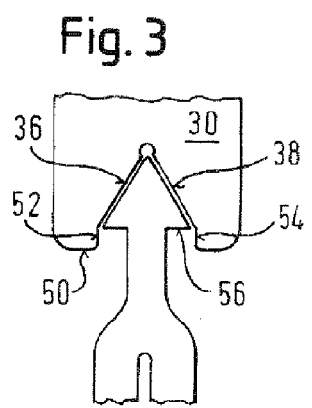
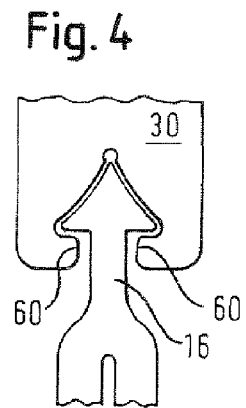
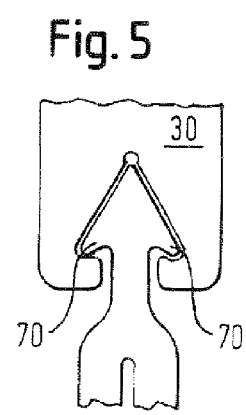
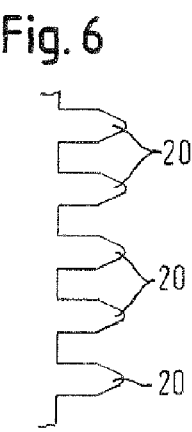
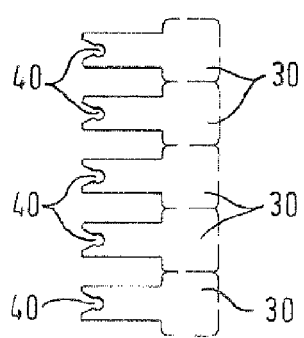

TUBULAR METAL PROSTHESIS AND METHOD OF MAKING IT

CROSS-REFERENCE TO RELATED APPLICATIONS

Incorporated herein by reference are International Application No. PCT/EP2007/057041 filed 10 Jul. 2007, published as WO 2008/006830 on 17 Jan. 2008 and GB application number 0616370.9 filed 10 Jul. 2006. This application is the national stage of and claims priority to PCT/EP2007/057041 filed 10 Jul. 2007 which claims priority to GB 0616370.9 filed 10 Jul. 2006, priority to which is also claimed.

TECHNICAL FIELD

This invention relates to a method of making a machined and polished tubular metal prosthesis that defines a lumen around a long axis of the prosthesis and to which is welded a component of another metal that has opposed major surfaces that are arcuate luminal and abluminal surfaces relative to said long axis.

BACKGROUND PRIOR ART

One disclosure of such a prosthesis is to be found in WO-A-02/15820 of the present applicant. The WO document discloses a self-expanding stent of nickel titanium shape memory alloy that carries a ring of spoons of tantalum at each end of the tube of the stent, these tantalum spoons serving as radiopaque markers so that the stent prosthesis can be located by radiographic techniques, when inside the body of a patient.

It is customary to polish a prosthesis during manufacture, prior to implantation in the body, for the obvious reason that, at the moment of implantation, there should be no surfaces in a condition of anything less than full integrity. Polishing is conventionally accomplished by an electro-polishing procedure and, in electro-polishing, the rate of removal of solid material from the surface being polished will vary, according to the chemical composition of the surface and the chemical composition of the fluid medium in contact with that surface. For example, in the case of a NITINOL nickel titanium memory metal stent with tantalum radiopaque markers, electropolishing can remove NITINOL four times as fast as it removes tantalum. Indeed, the present inventors have recognised a problem with electro-polishing a prosthesis such as the one disclosed in the WO document because, for any given electrolyte, the rate of electro-polishing of the tantalum spoon is liable to be substantially different from the rate of polishing of the nickel titanium prosthesis material.

Polishing the tantalum spoon separate from the nickel titanium stent matrix would be one way to manage the rate of removal of material from the surface being polished. However, electro-polishing is always liable to introduce some uncertainty as to the precise dimensions of the polished workpiece. Thus, when two components of a workpiece are to be approximated precisely, and then welded together, any electro-polishing prior to welding is liable to detract from the precision of placement of the respective components each side of the welding interface. Any such loss of precision can reduce the level of confidence in the integrity of the weld because, ideally, the gap between the components at the welding interface, to be filled by weld metal, should be precisely defined, and constant.

How, then, is one to reconcile integrity of the welded joint with precision polishing of the components of different metals? This is the problem that the present inventors addressed, and the present invention represents a solution to that problem.

In this specification, the word "polishing" covers any method of removing edges, surface roughness or imperfections. Electropolishing is one way. Chemical polishing, such as etching, is another. Mechanical polishing, such as tumbling or sand-blasting, is yet another.

SUMMARY OF THE INVENTION

In accordance with one aspect of the present invention, a method of making a prosthesis as stated above is characterised by the steps of 1) polishing at least one of the component and the prosthesis; 2) providing the respective complementary edge portions as ramp surfaces which, prior to said welding, can approach each other as the component moves in one direction along the long axis relative to the prosthesis, and can move away from each other, vice versa, when the component is moved in the opposite sense along the axis; 3) moving the component and the prosthesis relative to each other along the said axis, to approximate the respective ramp surfaces ready for welding; and 4) welding together the approximated ramp surfaces.

In another aspect of the present invention, a tubular metal prosthesis, such as is made by the method above, is characterised in that the complementary respective edge portions are ramp surfaces which (in the absence of welding) can approach each other as the component moves in one direction along the long axis relative to the prosthesis, and move away from each other vice versa when the component is moved in the opposite sense along the axis; and the ramp surfaces of at least one of the component and the prosthesis that receives the component exhibit polished surfaces.

It will appreciated that the ramp surfaces compensate for any variability in the amount of material removed from the complementary edge portions during polishing prior to welding, in that relative axial movement of the ramp surfaces with respect to each other can compensate for more or less removal of material from the ramp surfaces during polishing. It may be that the relative axial positions of the prosthesis, and the component welded to it after welding, vary to some extent but, in accordance with the invention, this is to be preferred over the situation where these relative axial positions are maintained constant, but at the cost of having a welding gap that varies according to the amount of material previously removed by polishing.

The reader will appreciate that some sort of tool or jig or clamp will be required, in order to support the prosthesis and component in approximated positions where the desired welding gap is presented for receipt of weld metal. The construction of any such tool, jig or clamp, is a matter for the skilled reader. Whereas optimal automated production of a stream of stents might require construction of a special tool, a more labour-intensive or custom-welding procedure would present no difficulties for a stent manufacturer.

It is routine and conventional these days to machine a metal prosthesis from a tube of raw material. One way is by etching procedures, for example, when the tube is of stainless steel. However, laser cutting of a stent matrix in the cylindrical wall of the tubular workpiece is by now an intensively used and well-understood method for making a metal prosthesis such as a self-expanding stent out of a tubular raw material such as nickel titanium shape memory alloy (NITINOL trade mark). For the skilled stent manufacturer, therefore, it is not a matter of difficulty to program the laser cutter to provide ramp surfaces in complementary edge portions of a tubular metal prosthesis and a component to be welded to that prosthesis.

The tantalum spoons of the above-mentioned WO document have edge portions that complement corresponding edge portions on the nickel titanium stent, with the portions each side of the welding interface having a recognisable male/female relationship, and with the female portion being exhibited on the radiopaque tantalum marker spoons or other component to be welded to the prosthesis. Such a male/female relationship is visualised for the ramp surfaces of the present invention. Indeed, it is envisaged that the male portion would exhibit an arrowhead shape with a tip at one end and a shank at the other and that the component with the female edge portions would exhibit at least one re-entrant portion for engaging behind the arrowhead of the male portion.

BRIEF DESCRIPTION OF THE DRAWINGS

For a better understanding of the present invention, and to show how the same may be carried into effect, reference will now be made, be way of example, to the accompanying drawings, in which:

FIG. 1 is a perspective view of a single welding interface between part of a tubular metal prosthesis and a component of a different metal to be welded to that prosthesis FIGS. 2 to 5 show, respectively, plan views of four variations on the design concept visible in FIG. 1;

FIG. 6 shows part of a ring of male portions that extends around the circumference of a tubular metal prosthesis; and FIG. 7 shows (at slightly higher magnification) part of a ring of corresponding components of another metal, with female portions destined to be welded to the respective projecting male portions shown in FIG. 6.

DETAILED DESCRIPTION

Referring to FIG. 1, a stent 10 similar to the one shown in WO-A-02/15820 has, at each end, a ring of nodes 12 between adjacent struts 14, 15 of the strut matrix of the stent. A shank 16 extends axially away from each node 12 and the stent matrix as such, as far as the root 18 of an arrowhead shape 20 that lies between symmetrical and complementary ramp surfaces 22 and 24 that converge to a tip 26 of the arrowhead 20 to define a male portion that is approximated with a female portion of a tantalum marker spoon 30 that has an abluminal major surface 32 and (not visible in FIG. 1) an opposed luminal major surface 34 which faces the long axis of the stent tube so that the thickness of the tantalum spoon 30 lies within an annulus centered on the long axis of the stent.

The female portion that receives the arrowhead 20 is provided by opposed symmetrical complementary ramp surfaces 36 and 38 which converge to the root or base 40 of what can be seen as a V-shaped recess to receive the ramp surfaces 22 an 24 of the arrowhead 20. At the base of the groove 40 there is a cylindrical throughbore 42 which is provided for reducing the risk of crack-initiation and propagation from the root of the V-shaped groove that receives the arrowhead 20.

In manufacture, the stent matrix (typically made of nickel titanium shape memory alloy) is electro-polished before it is approximated with the tantalum spoon 30. Likewise, the tantalum spoon 30, likely still part of a laser cut tube of tantalum and in the company of a plurality of other tantalum spoons that extends around the axis of the tubular workpiece (see the description in WO-A-02/15820) is also electro-polished and, after separate electro-polishing of the tantalum components and the nickel titanium components, the respective arrowhead male portions 20 can be brought into approximation with the corresponding female ramp surfaces of the respective tantalum spoons 30, ready for welding.

FIG. 1 does reveal a small welding gap between ramp surfaces 22 and 36, and surfaces 24 and 38. This is the gap that is filled with weld metal in consequence of the welding step of assembly of the tantalum spoons 30 to the stent prosthesis 10. If the amount of material removed from the respective ramp surfaces during respective electro-polishing is different form what was predicted, this need have no disturbing effect on the desired welding gap, provided that prior to welding there is a judicious relative axial movement of the male and female portions so as to bring about the desired optimal welding gap between the respective ramp surfaces.

Turning now to the remaining drawing Figures, FIG. 2 is provided with reference numbers corresponding to those of FIG. 1 and, we think, needs no further text description. FIG. 3 differs only slightly from FIG. 2, in that the female ramp surfaces do not run as far as the marginal edge of the tantalum component. Rather, the ramp surfaces are set back from the edge 50, in that the ramp surface 36 continues as an unramped axially aligned edge 52 and, likewise, ramp surface 38 continues as an axially aligned straight edge 54, parallel to edge 52. Recessing the arrowhead "inside" the tantalum spoon avoids any adverse effects that might flow from having the acute angle between the arrowhead ramp surfaces 22 and 24 and the base 56 of the arrowhead lying outside the envelope of the tantalum spoon 30.

Turning to FIG. 4, there is shown two further variations. First, the ramp surfaces are arcuate rather than straight, so the welding gap is not mathematically constant but nevertheless changes with relative axial movement of the ramp surfaces and, second, the arrowhead is gripped by re-entrant portions 60 that flank the shank 16. This engagement can be, as a matter of design preference, either resilient or of form-fit conception, with the arrowhead being introduced from radially inside or outside the female receiving portion in the component 30.

FIG. 5 reveals a further variation, and difference from FIG. 4, in that the arrowhead shape includes two terminal barbs 70 which can be resilient enough to locate the arrowhead with the cavity in the spoon 30. From FIGS. 6 and 7 it will be appreciated that a ring of male projections 20 can be located around the circumference of the prosthesis, and offered up to a corresponding ring of recesses, each with root 40, in respective components of another metal such as spoons 30. Just as in WO 02/15820 mentioned above, the ring of spoons can constitute a complete ring of material around the lumen of the prosthesis, with only laser cut gaps in between adjacent spoons.

In the case of welding a plurality of components (such as radiopaque markers) to a prosthesis, the components can be found all within a common workpiece, from which they are parted after welding, as described above. Alternatively, each component can be separate from the outset, then prepared individually, and then welded individually to the prosthesis.

It will be appreciated that the prosthesis needs to be polished to a high level and, generally speaking, the excellence and integrity of the polishing of the prosthesis overall should, if anything, be higher than the level of polishing of a radiopaque marker on the prosthesis.

The ramp surfaces that characterize the present invention can compensate for variations, prior to welding, in the weld surfaces of the prosthesis and component, respectively.

The foregoing embodiments are presented by way of example only; the scope of the present invention is to be limited only by the following claims.

The invention claimed is:

1. A tubular metal stent, comprising:
   a stent body formed from a first material, including:
   a first stent ring including struts connected by nodes positioned at a first end of the stent body,
   a plurality of shanks extending axially away from nodes on the first stent ring along a longitudinal axis of the stent body,
   each of the plurality of shanks having a head portion extending therefrom,
   each head portion including first and second polished ramp surfaces converging and meeting at a point axially away from the stent body; and
   a plurality of radiopaque markers formed from a second material different from the first material, each of the markers including an end recess having complementary polished third and fourth ramp surfaces that abut the polished first and second ramp surfaces when the head portion is inserted into the end recess, wherein the end recess of each of the radiopaque markers includes axially aligned edges parallel to the longitudinal axis of the stent body adjacent the polished third and fourth ramp surfaces.

2. The stent according to claim 1, further comprising a second stent ring including struts connected by nodes positioned at a second end of the stent body opposite the first end of the stent body.

3. The stent according to claim 2, further comprising a plurality of shanks extending axially away from nodes on the second stent ring along a longitudinal axis of the stent body, each of the plurality of shanks having a head portion extending therefrom.

4. The stent according to claim 3, wherein each head portion includes first and second polished ramp surfaces converging and meeting at a point axially away from the stent body.

5. The stent according to claim 1, wherein each of the radiopaque markers further comprises a cylindrical throughbore at an end of the recess.

6. The stent according to claim 1, wherein the head portion polished first and second ramp surfaces and end recess complementary polished third and fourth ramp surfaces have an arcuate shape.

* * * * *